(12) United States Patent
Sefton et al.

(10) Patent No.: US 6,641,832 B2
(45) Date of Patent: *Nov. 4, 2003

(54) INCREASING BLOOD FLOW TO TISSUE WITH ANGIOGENIC MATERIAL CONTAINING POLYMER AND VASCULARIZING COMPOUND

(76) Inventors: Michael Vivian Sefton, 67 Elm Ridge Drive, Toronto (CA), M6B 1A2; Julia Elizabeth Babensee, 2409 Reserve Dr., Atlanta, GA (US) 30319; Michael Humphrey May, 9 Terrance Drive, Brantford, Ont (CA), N3R 3G2

( * ) Notice: Subject to any disclaimer, the term of this patent is extended or adjusted under 35 U.S.C. 154(b) by 0 days.

This patent is subject to a terminal disclaimer.

(21) Appl. No.: 09/739,662

(22) Filed: Dec. 20, 2000

(65) Prior Publication Data

US 2002/0037308 A1 Mar. 28, 2002

Related U.S. Application Data

(62) Division of application No. 09/069,544, filed on Apr. 30, 1998, now Pat. No. 6,261,585, which is a continuation of application No. PCT/CA96/00725, filed on Oct. 31, 1996.

(30) Foreign Application Priority Data

Oct. 31, 1995 (CA) .............................................. 2161863

(51) Int. Cl.$^7$ ......................... A61F 13/00; A61L 15/00; C12N 11/04; C12N 5/06; C12N 5/08
(52) U.S. Cl. ..................... 424/423; 424/443; 424/445; 424/486; 424/489; 424/78.08; 424/78.31; 424/93.7; 435/177; 435/182; 435/382; 435/395
(58) Field of Search ................................. 435/174, 177, 435/180, 182, 382, 395; 424/422, 423, 443, 445, 486, 489, 501, 93.7, 78.08, 78.31

(56) References Cited

U.S. PATENT DOCUMENTS 4,353,888 A * 10/1982 Sefton ......................... 424/25
6,261,585 B1 * 7/2001 Sefton et al. ................ 424/423

OTHER PUBLICATIONS

Sefton, et al., "Microencapsulation of live animal cells using polyacrylates", Adv. Polym. Sci., vol. 107, 1993, pp. 146–197.*
Uludag, H. et al., "Microencapsulated human hepatoma (HepG2) cells: capsule–to–capsule variations in protein secretion and permeability" Journal of Controlled Release, Feb. 1/95, vol. 33, No. 22, pp. 273–283.*
Sefton, M.V. et al., "Controlled release using microencapsulated mammalian cells", Journal of Controlled Release, vol. 19, Mar. 1992, No. 1, pp. 289–297.*
Crooks et al., Microencapsulation of mammalian cells in a HEMA–MMA copolymer: Effects on capsule morphology and permeability, Journal of Biomedical Materials Research, vol. 24, 1990, pp. 1241–1262.*
Uludag, H. et al., "Viability and Protein Secretion from Human Hepatoma (HepG2) Cells Encapsulated in 400–$\mu$m Polyacrylate Microcapsules by Submerged Nozzle–Liquid Jet Extrusion", Biotechnology and Bioengineering, vol. 44, 1994, pp. 1199–1204.*

* cited by examiner

Primary Examiner—David M. Naff
(74) Attorney, Agent, or Firm—Riches, McKenzie & Herbert LLP (57) ABSTRACT

An angiogenic material is prepared which promotes extensive vascularization when implanted in animal tissue. The angiogenic material is preferably used in microcapsule coatings and microspheres for implantation in animals. In microcapsules, the angiogenic material promotes better exchange of nutrients, waste products and cellular products between encapsulated cells and the circulatory system of the host animal. Preferably, the angiogenic material consists of a biocompatible polymer and a vascularizing compound consisting of polymerizable compounds capable of forming anions. Microspheres containing the angiogenic material may be used to assist in recovery of ischemic heart muscle by injection of the microspheres into the heart muscle or blood vessels serving the ischemic area. Also disclosed is a method of forming small microcapsules and microspheres by passing cell aggregates or air bubbles through layers of a density gradient.

30 Claims, 3 Drawing Sheets

INCREASING BLOOD FLOW TO TISSUE WITH ANGIOGENIC MATERIAL CONTAINING POLYMER AND VASCULARIZING COMPOUND

RELATED APPLICATIONS

This application is a divisional application of applicants' pending U.S. patent application Ser. No. 09/069,544 filed on Apr. 30, 1998, now U.S. Pat. No. 6,261,585, as a continuation application of PCT International patent application Serial No. PCT/CA96/00725 designating the United States, filed on Oct. 31, 1996.

FIELD OF THE INVENTION

This invention relates to a material with blood vessel generating properties, uses thereof for encapsulating cells within microcapsules and for forming microspheres, and a method for forming small microspheres and microcapsules.

BACKGROUND OF THE INVENTION

There are certain situations where it is desirable to vascularize (to form blood vessels in) the tissue of a living animal.

One such situation is in the treatment of heart muscle after an infarction, or heart attack. Depending on the severity of the infarction, some of the heart muscle will be damaged ("ischemic") because of the inability of the remaining coronary blood supply to provide enough oxygen and nutrients to it.

Considerable effort has been directed to the use of therapeutic agents such as basic fibroblast growth factor (bFGF) or V-endothelial growth factor (VEGF) (S. Takeshita et al, J. Clin Invest. 1994, 93: 662–670) to generate a collateral blood supply to damaged heart tissue after a period of ischemia and thereby aid in the recovery of the heart after a heart attack. These therapeutic agents are expensive, somewhat unstable and difficult to deliver and have some undesirable side effects. The disadvantage exists that the generation of new blood vessels in ischemic heart muscle is not presently possible without the use of drugs.

Another such situation in which vascularization is desirable is the treatment of peripheral ischemia that may result, for example, as a complication of Diabetes. The microcirculation supplying the peripheral tissue is not able to provide adequate oxygen and nutrients to the legs and feet which results in tissue death, susceptibility to infection, and eventually, amputation.

A further situation is in the treatment of various wounds, including severe burns, or chronic wounds such as bed sores or venous and diabetic ulcers. Chronic wounds are difficult to heal, partly due to an insufficient vascular bed supplying nutrients and healing factors to the wound site.

Another situation is the treatment of the healing interfaces between transplanted and host tissue. For example, the incorporation and survival of cadaverous gum tissue, implanted to replace diseased gum tissue, is hindered by a lack of blood vessels supplying the new tissue with nutrients.

Another situation in which it is desirable to generate new blood vessels is in the field of implantable drug delivery systems, such as microencapsulated animal cells which produce and release a therapeutic agent, such as a biologically active molecule, to the host in which they are implanted.

When any material or device is implanted in the body of an animal (as used herein, terms "animal" and "host" include humans), the body responds by producing what is termed a foreign body reaction. This involves various leukocytes, particularly macrophages and neutrophils, and typically results in an avascular fibrous capsule that is intended to isolate or "wall off" the material or device from the body.

This reaction is appropriate for many situations but not for implantable drug delivery systems, such as implantable microcapsules, where it is preferable to have blood vessels present close to the surface of the material comprising the delivery system. These blood vessels are then able to carry the therapeutic agent to parts of the body where it is needed. An avascular fibrous capsule formed around the drug delivery system acts as a diffusion barrier between the drug delivery system and the body's blood vessels, preventing or at least slowing the delivery of the therapeutic agent.

The development of fibrogenic tissue around microcapsules has been a persistent and fatal problem with prior art drug delivery systems utilizing microcapsules. In order to survive, implanted cells require free diffusion of nutrients, gases, and waste products while releasing to the host the intended cellular product produced by the microencapsulated cells. However, the formation of scar tissue and lack of vascularization leave the implanted cells effectively cut off from the nutrients necessary for their survival. Therefore, a disadvantage exists that no drug delivery systems utilizing implanted microcapsules are known to date which are vascularized (i.e., create blood vessels in the surrounding tissue in the immediate vicinity of the capsules) when implanted into a host animal.

In order to further promote effective diffusion of essential nutrients, toxic metabolic end-products and cellular products through the microcapsule wall, it is preferred that cells be encapsulated in small microcapsules (defined as microcapsules less than 500 $\mu$m in diameter) because of their high surface area and thin walls.

Various techniques have been used for encapsulating mammalian cells in small microcapsules. For example, alginate-polylysine microcapsules having diameters between 250 $\mu$m and 350 $\mu$m have been prepared with an electrostatic droplet generator, as reported by Sun et al., *ASAIO J.* 38:125–127 (1992) and Hallé et al., *Transplant. Proc.* 24:2930–2932 (1992). Alginate-polylysine microcapsules having a diameter of less than 500 $\mu$m have been produced with an air-jet droplet generator as reported by Wolters et al., *J. Appl. Biomat.* 3:281–286 (1992).

Zekorn et al., *Acta Diabetol.* 29:41–45 (1992), describe a method of encapsulation where pancreatic islets are centrifuged through an alginate solution and a $Ba^{++}$ containing medium, which yields alginate-coated islets, the "capsules" having roughly the same size as individual islets and, thereby, effectively eliminating any void volume. There was allegedly no impairment of insulin transport through the alginate coat, although the effect of an additional layer of polylysine was not determined. An interfacial photopolymerization process was reported by Pathak et al., *J. Am. Chem. Soc.* 114:8311–8312 (1991), for encapsulating pancreatic islets in polyethylene glycol based polymeric microcapsule having a diameter of 500 $\mu$m, or for conformal coating as described by Cruise et al., *Trans. 19th Ann. Meet. Soc. Biomat.* (*USA*) Abstract 205 (1993). Water insoluble polymers cannot be used as membrane materials by either of these conformal coating/microencapsulation methods.

Encapsulation of mammalian cells in water insoluble synthetic polymer, polyacrylate, for example, by an interfacial precipitation process is described by Sefton and Stevenson, *Adv. Polym. Sci.* 107:143–197 (1993). Retention of cell viability in vitro and secretion of several bioactive agents have been demonstrated in hydroxyethyl methacrylate-methyl methacrylate (HEMA-MMA) microcapsules with diameters of approximately 750 µm by Babensee et al., J. Biomed. Mat. Res. 26:1401–1418 (1992), Uludag and Sefton, J. Biomed. Mat. Res. 27:1213–1224 (1993), and Uludag et al., J. Controll. Rel. 24:3–12 (1993). A limitation of this method is that smaller microcapsules cannot be produced due to the relatively low droplet-shearing force as reported by Crooks et al., J. Biomed. Mat. Res. 24:1241–1262, (1990).

However, the disadvantage exists that prior art methods of making microcapsules less than 500 µm in diameter are not particularly efficient. There is still a need for methods which not only produce small diameter microcapsules, but also produce them efficiently, consistently, and with predictable properties.

SUMMARY OF THE INVENTION

To at least partially overcome the above disadvantages, the present invention provides an angiogenic material containing a component which causes the generation of blood vessels in surrounding tissue.

Preferably, the angiogenic material comprises a biocompatible polymer and a vascularizing compound, the vascularizing compound preferably being introduced into the biocompatible polymer at the time of polymerization. Because of its biocompatibility, the angiogenic material of the present invention, when implanted in the tissue of a host animal, generates a minimal inflammatory or foreign body reaction in the surrounding tissue. This has the beneficial effect of minimizing the production of inhibitors of growth factors and of angiogenesis more generally. The result is minimization of the avascular fibrous capsule around the angiogenic material and maximization of the capacity of the host to produce the desired blood vessels in the vicinity of the angiogenic material.

Preferably, the vascularizing compound is a polymerizable compound which has anionic character in the final polymer when implanted, for example, polymerizable compounds having ionizable groups such as sulfate, sulfonic acid and carboxylic acid groups. More preferred are polymerizable acids such as acrylic acid, methacrylic acid, crotonic acid, itaconic acid, vinylsulfonic acid and vinylacetic acid, most preferably methacrylic acid. The vascularizing compound, when incorporated in the biocompatible polymer to form the angiogenic material of the present invention, is believed to act as a sink for blood vessel generating growth factors such as VEGF or bFGF. These growth factors are then slowly released by the angiogenic material. As a result of this long release period, blood vessels produced in the vicinity of the angiogenic material are sustained.

In one embodiment of the invention, the angiogenic material is implanted into ischemic heart muscle or in blood vessels close to the heart to stimulate the growth of blood vessels in the ischemic tissue. The angiogenic material may preferably be implanted in the form of a disk, fibre or microsphere, with microsphere being the most preferred form. Preferably, the microsphere has a diameter no greater than about 500 µm, more preferably no greater than about 200 µm, and most preferably from less than about 10 µm to about 50 µm.

In another embodiment, the angiogenic material is implanted into the peripheral ischemic tissue or in blood vessels close to the ischemic tissue to stimulate the growth of blood vessels into the tissue. As with heart tissue, the angiogenic material may preferably be implanted in the form of a disk, fiber or microsphere, with microspheres having the above diameters being the most preferred form.

In another embodiment, the angiogenic material is incorporated into a wound care product applied to the surface of a wound such as a chronic wound or burn. The wound care product may be composed of the angiogenic material or the angiogenic material may be a separate component dispersed in the wound care product in the form of microspheres, disks, or fibers. Wound care products may be wet dressings, dry dressings, occlusive dressings, non-occlusive dressings, wound pastes, or any other product applied to a wound.

In another embodiment, the angiogenic material is placed at the interface between transplanted and host tissue to stimulate growth of host vessels into the transplant to encourage incorporation of the tissue and to supply it with oxygen and nutrients. The angiogenic material may preferably be in the form of small microspheres or fibers, a thin film applied between the new and existing tissue, or at the suture lines.

In another embodiment, the angiogenic material of the present invention is incorporated in the coating of a microcapsule containing cells and/or cell aggregates which, when the microcapsule is implanted in the body of a host, release a cellular product to the host. Microcapsules containing the angiogenic material of the present invention cause generation of blood vessels in tissue surrounding the microcapsule, resulting in more efficient diffusion of cellular products and waste products from the encapsulated cells and better diffusion of nutrients and gases to the encapsulated cells. To further improve efficiency of diffusion, microcapsules of the present invention are preferably no greater than 500 µm in diameter.

The present invention also provides a new method for forming polymeric microspheres and microcapsules encapsulating mammalian cells. This method is particularly useful for formation of microcapsules and microspheres having diameters no greater than about 500 µm. However, it is to be understood that the method of the present invention may be used to prepare microcapsules and microspheres of any suitable dimension.

In the method of the present invention, at least three liquid layers are loaded into a coating chamber to form a density gradient. The three liquid layers are, in order of exposure by the cells, a polymer solution layer containing a coating polymer, a solvent layer and a non-solvent layer. A cell aggregate suspension is introduced at the top or bottom (depending on the density of the aggregates relative to the liquid density gradient) of the coating chamber, centrifugal force is preferably applied, and the conformally coated cell aggregates are removed from the opposite end of the coating chamber.

Preferably, the density gradient comprises five liquid layers, with solvent and non-solvent layers being arranged symmetrically about the polymer solution layer. This allows the density gradient to accommodate cell aggregates with densities either greater than or less than the density gradient layers. Preferably, the liquid layers of the density gradient are, in order from bottom to top: a lower non-solvent layer, a lower solvent layer more dense than the polymer solution, a polymer solution layer containing a coating polymer, an upper solvent layer less dense than the polymer solution layer, and an upper non-solvent layer. The final non-solvent layer into which the aggregates pass is where precipitation of the polymer coating occurs, and is, therefore, also called the precipitation solution layer. Preferably, the upper and lower non-solvent layers are aqueous so that cells enter and exit the coating chamber under aqueous conditions.

Preferred polymers suitable for use in the polymer solution layer include any water insoluble, biocompatible polymer that precipitates in an aqueous environment and is semipermeable after fully precipitating.

In another embodiment of the process of the present invention, microspheres are produced using density gradient layers in a coating chamber as discussed above. However, instead of introducing cell aggregates into the coating chamber, fine gas bubbles are introduced into the polymer solution layer, from which they rise into the upper solvent layer and finally into the upper non-solvent, precipitating layer. Air is the preferred gas because it need not be fed into the coating chamber in a non-solvent suspension and it allows the number of layers in the density gradient to be reduced to three.

The disclosed microcapsules or microspheres can be administered to animals by various means, including implantation, injection, and infusion, via cannulas, catheters, pipette or directly through a needle from a syringe or using forceps or a trocar. When implanted into animals the microcapsules and microspheres according to the present invention will become surrounded with well vascularized tissue.

It is therefore an object of this invention to provide an angiogenic material, which when implanted into tissue of a host animal, promotes growth of blood vessels in the tissue.

It is a further object of this invention to provide microcapsules which promote vascularization of the microcapsules when implanted into a host animal.

It is a further object of this invention to provide microspheres of a material that promotes new blood vessel growth when introduced into heart muscle of a host animal.

It is a further object of this invention to provide an improved method for producing microcapsules and microspheres.

It is a further object of this invention to provide an improved method for producing microcapsules and microspheres having a diameter no greater than 500 µm.

It is a further object of this invention to provide a method of controllably producing small microcapsules with thin walls allowing free diffusion of gases, nutrients and small biologically active molecules.

Accordingly, in one aspect, the present invention provides a method of conformally coating cell aggregates, comprising the following three steps:
  a) loading liquid layers into a coating chamber to form a density gradient, wherein the liquid layers comprise in order from bottom to top: a lower non-solvent layer, a lower solvent layer, a polymer solution layer containing a coating polymer, an upper solvent layer, and an upper non-solvent layer;
  b) introducing cell aggregates into one of the non-solvent layers of the density gradient; and
  c) applying centrifugal force to the coating chamber, such that the cell aggregates pass through each of the liquid layers of the density gradient and thereby become conformally coated by a layer of the coating polymer, wherein said solvent layers contain a solvent capable of dissolving said coating polymer and said coating polymer is substantially insoluble in said non-solvent layers.

In a "sinking cell" system, the cell aggregates have a density greater than a density of each of the liquid layers of the density gradient, such that the cell aggregates sink downwardly through each of the liquid layers of the density gradient. Conversely, in a "rising cell" system, the cell aggregates have a density less than a density of each of the liquid layers of the density gradient, such that the cell aggregates rise upwardly through each of the liquid layers of the density gradient.

The order of steps (a) and (b) in the above method may be reversed so that the cell aggregates are introduced into a bottom of the coating chamber before loading of the liquid layers of the density gradient into the coating chamber.

Preferably, the solvent layers contain a solvent which is the same as a solvent in which the coating polymer is dissolved in the polymer solution layer, the non-solvent layers each comprise an aqueous solution and the cell aggregates are introduced into the coating chamber in the form of an aqueous suspension.

Preferably, the conformally coated cell aggregates have a diameter of not greater than about 500 µm.

Preferably, the coating polymer comprises a biocompatible, water-insoluble polymer which precipitates in an aqueous environment and is semi-permeable after precipitation.

Preferably, the coating polymer additionally comprises a vascularizing compound which, when the conformally coated cell aggregates are implanted into tissue of an animal, promotes generation of blood vessels in the immediate vicinity of the implanted conformally coated cell aggregates.

Preferably, said coating polymer is selected from the group comprising polyacrylates, more preferably the polymer solution comprises a solution of hydroxyethyl methacrylate-methyl methacrylate in polyethylene glycol.

In another aspect, the present invention provides a method of producing microspheres, comprising the following steps:
  a) loading liquid layers into a coating chamber to form a density gradient, the liquid layers comprising, in order from bottom to top: a polymer solution layer containing a coating polymer, a solvent layer and a non-solvent layer, said solvent layer containing a solvent capable of dissolving said coating polymer and said coating polymer being substantially insoluble in said non-solvent layer;
  b) introducing gas bubbles into the polymer solution layer; and
  c) allowing the bubbles to rise through each liquid layer of the density gradient so that the bubbles become coated by a layer of the coating polymer to form microspheres.

As in the case of microcapsules, the solvent layer preferably contains a solvent which is the same as a solvent in which the coating polymer is dissolved in the polymer solution layer and the non-solvent layer comprises an aqueous solution.

Preferably, the microspheres have a diameter of not greater than about 200 µm and the coating polymer comprises a biocompatible, water-insoluble polymer which precipitates in an aqueous environment.

Preferably, the coating polymer additionally comprises a vascularizing compound which, when the microspheres are implanted into tissue of an animal, promotes generation of blood vessels in the immediate vicinity of the microspheres.

Preferably, the polymer solution comprises a solution of hydroxyethyl methacrylate-methyl methacrylate in polyethylene glycol; said solvent layer comprises polyethylene glycol; said non-solvent layer comprises distilled water; and said gas bubbles comprise bubbles of air.

In another aspect, the present invention provides a microcapsule comprising: a core containing cellular material selected from one or both of cells and cell aggregates; and a conformal, semi-permeable coating of angiogenic material over the core, the angiogenic material comprising a biocompatible polymer and a vascularizing compound selected from the group comprising polymerizable compounds capable of forming anions, wherein, when implanted in animal tissue, said microcapsule promotes generation of blood vessels in its immediate vicinity and induces minimal or no fibrous capsule formation.

Preferably, the core of the microcapsule additionally comprises a bioactive compound selected from the group comprising growth factors, attachment matrices and immobilization matrices, and the cellular material comprises mammalian cells which produce a bioactive cellular product.

Preferably, the said biocompatible polymer is selected from the group comprising polyacrylates and the vascularization compound comprises a polymerizable compound containing an ionizable group selected from the group comprising sulfates, sulfonic acid groups and carboxyl groups, more preferably acrylic acid, methacrylic acid, crotonic acid, itaconic acid, vinylsulfonic acid and vinylacetic acid, and most preferably methacrylic acid which is incorporated into the biocompatible polymer at the time of polymerization.

Preferably, the microcapsule has a diameter of no more than about 500 µm.

In yet another aspect, the present invention provides an angiogenic material comprising a biocompatible polymer and a vascularizing compound selected from the group comprising polymerizable compounds capable of forming anions; wherein, when implanted in animal tissue, said angiogenic material promotes generation of blood vessels in its immediate vicinity and induces minimal or no fibrous capsule formation.

Preferably, the angiogenic material is in the form of a microsphere having a diameter of less than about 200 µm.

Preferably, the biocompatible polymer is selected from the group comprising polyacrylates and the vascularization compound comprises a polymerizable compound containing an ionizable group selected from the group comprising sulfates, sulfonic acid groups and carboxyl groups, more preferably acrylic acid, methacrylic acid, crotonic acid, itaconic acid, vinylsulfonic acid and vinylacetic acid, and most preferably methacrylic acid which is incorporated into the biocompatible polymer at the time of polymerization.

In yet another aspect, the present invention provides the use of microspheres comprising an angiogenic material for increasing blood flow to ischemic heart muscle, wherein: said microspheres are implanted into the ischemic heart muscle or blood vessels in the immediate vicinity of the ischemic heart muscle, said microspheres having a diameter of from less than about 10 µm to about 50 µm, said angiogenic material comprising a biocompatible polymer and a vascularizing compound selected from the group comprising polymerizable compounds capable of forming anions and which promote the growth of blood vessels, which, when implanted in animal tissue, said angiogenic material promotes generation of blood vessels in its immediate vicinity and induces minimal or no fibrous capsule formation.

Preferably, the vascularization compound comprises a polymerizable compound containing an ionizable group selected from the group comprising sulfates, sulfonic acid groups and carboxyl groups, more preferably acrylic acid, methacrylic acid, crotonic acid, itaconic acid, vinylsulfonic acid and vinylacetic acid, most preferably methacrylic acid which is incorporated into the biocompatible polymer at the time of polymerization.

Preferably, the biocompatible polymer is selected from the group comprising polyacrylates.

DETAILED DESCRIPTION OF THE INVENTION

Preferred angiogenic materials of the present invention are now discussed below in terms of their preferred uses, namely for use in the formation of microcapsules and microspheres for implantation into a host animal.

1. Angiogenic Material

The angiogenic material of the present invention is of a composition which, when implanted into an animal host, results in the formation of vascularized tissue in its immediate vicinity. Preferred applications for the angiogenic materials according to the present invention include vascularization of ischemic tissue such as ischemic heart tissue and ischemic peripheral tissue, and vascularization of chronic wounds, burns and transplanted tissue.

Preferably, the angiogenic material comprises a biocompatible polymer and a vascularizing compound. The vascularizing compound is preferably incorporated into the biocompatible polymer, in an amount effective to cause vascularization, at the time of polymerization of the biocompatible polymer.

Biocompatible polymers are defined herein as polymers that induce, when implanted, an appropriate host response given the application. For the applications of primary interest here (drug delivery systems, microencapsulated cells, angiogenic microspheres), biocompatible polymers are those which are nontoxic, noninflammatory, non immunogenic, non carcinogenic, do not activate complement, leukocytes or other blood cells, induce minimal or no fibrous capsule formation, and minimal generation of activated macrophages or other components of the inflammatory response.

Preferred biocompatible polymers for use in the present invention include polyacrylates, polyphosphazenes, various vinyl polymers including polyvinyl chloride, polyacrylonitrile, polyvinyl acetate, ethylene vinyl acetate, polyvinyl alcohol copolymers, polyvinyl amine copolymers, polyimides, polyether ketones, polysulphones, siloxanes, polyurethanes and polyamides, polycarbonates, polyesters and bioresorbables such as polyanhydrides, polyorthoesters, polycaprolactones, polyamino acids, polylactic/glycolic acid copolymers and polyhydroxybutyrates. More preferred biocompatible polymers are polyacrylates, with hydroxyethyl methacrylate-methyl methacrylate (HEMA-MMA) and hydroxyethyl methacrylate-methyl methacrylate-methacrylic acid (HEMA-MMA-MAA) being particularly preferred.

The term "vascularizing compound" as used herein refers to a compound which, when incorporated into the outer polymeric wall of a microcapsule or microsphere, increases the level of vascularization of the microcapsule or microsphere when implanted, relative to the level of vascularization of an implanted microcapsule or microsphere lacking the compound. The term "vascularization" as used herein refers to the blood vessel network around an implanted microcapsule or microsphere, or the formation of such a blood vessel network.

Preferred vascularization compounds according to the present invention are polymerizable compounds containing groups capable of forming anions, such as sulfate, sulfonic acid and carboxylic acid groups. More preferred are polymerizable acids such as acrylic acid, methacrylic acid, crotonic acid, itaconic acid, vinylsulfonic acid and vinylacetic acid, with methacrylic acid being most preferred. The inventors have found that increasing the concentration of methacrylic acid incorporated into microcapsules increases the amount of vascularization.

2. Microcapsules

The term "microcapsule" as used herein refers to any polymeric membrane that encloses an interior core of a different material. Preferred microcapsules according to the present invention comprise cell aggregates conformally coated with a polymeric membrane which contains the angiogenic material of the present invention. Microcapsules of the present invention are preferably no more than 500 µm in diameter.

Vascularization of tissue surrounding a microcapsule connects the implanted cells with the distribution system of the animal. The host animal's blood system then delivers nutrients to the implanted cells and carries away metabolic waste products and cellular products.

Preferably, the cells encapsulated in a microcapsule of the present invention are mammalian cells. The cells can be in the form of individual cells, grouped in cell aggregates or tissue fragments. The term "cell aggregate" as used herein refers to any group of cells which form a coherent mass. Such cell aggregates include, for example, individual cells which have clumped together and groups of cells which retain their natural association, such as an organ fragment like a pancreatic islet of Langerhans.

Preferred cells are mammalian cells that produce a desired cellular product. The term "cellular product" as used herein refers to any molecule secreted or released from a cell. Preferably, such molecules are biologically active compounds, such as therapeutic agents.

More preferably, the encapsulated cells are parenchymal cells, such as hepatic cells or islet cells. The cells may be genetically modified using techniques which are well known to those skilled in the art.

Bioactive compounds are preferably encapsulated with the cells or incorporated into the polymeric membrane of the microcapsule. The term "bioactive compound" as used herein refers to any compound that enhances cell viability or promotes cell growth. Examples of bioactive compounds include: growth factors such as epidermal growth factor (EGF), basic fibroblast growth factor (bFGF), nerve growth factor (NGF) and transforming growth factor beta (TGFβ); attachment matrices such as collagen, laminin and/or fibronectin; and immobilization matrices such as agarose, alginate or chitosan. Although immobilization matrices do not possess specific biological activity, they have the ability to limit cell density and control cell distribution, which has the effect of enhancing cell viability.

Preferably, the bioactive compound used in the microcapsules of the present invention is an attachment matrix. A preferred attachment matrix is Matrigel®, available from Collaborative Research, Bedford, Mass. Matrigel is a mixture of laminin (60%), type IV collagen (30%), heparin sulfate proteoglycan (3%), nidogen (5%) and entactin (<1%). Another preferred matrix is collagen type IV.

Including an attachment matrix in the microcapsule core allows encapsulated attachment dependent cells to grow, thereby increasing the density of encapsulated cells. Incorporation or encapsulation of other bioactive compounds in a microcapsule can be used to stimulate growth of the encapsulated cells or promote the retention of their differentiated or functional state.

Bioactive compounds are incorporated into the microcapsule during formation of the microcapsule. This is easily accomplished by including the bioactive compound in the cell suspension or the polymer solution used in making the microcapsule.

3. Microspheres

The term "microsphere" as used herein refers to a polymeric sphere of microscopic dimensions, i.e. less than 1 mm and preferably less than 200 µm in diameter and more than 0.1 µm in diameter. Microspheres according to the present invention may be solid, hollow or may contain growth factors or other biologically active components. Particularly preferred microspheres according to the present invention comprise the angiogenic material of the present invention and have a diameter of from less than about 10 µm to about 50 µm.

In one preferred embodiment, the microspheres of the present invention are used to aid in the recovery of ischemic heart muscle. To accomplish this, microspheres of about 10 to 50 µm diameter are preferably infused into the artery feeding the ischemic area or the vein draining the area, as close to the site of ischemia as possible. The microspheres become lodged in one or more of the narrow vessels perfusing the ischemic area and induce the development of a collateral circulation which enhances the delivery of oxygen and nutrients to the ischemic heart muscle.

Alternatively, microspheres of less than about 10 µm may preferably be injected directly into the heart muscle to produce the same effect.

Vascularization around the implanted microspheres results in improved oxygen and nutrient supply to ischemic tissue, thereby enabling it to recover and restore its normal function: e.g., heart muscle contraction.

As discussed above, microspheres according to the present invention may also be used to stimulate growth of blood vessels in other ischemic tissues such as peripheral ischemic tissue, and to stimulate growth of blood vessels in chronic wounds, burns and transplanted tissue.

4. Formation of Microcapsules by Conformal Coating Microencapsulation

In the method of the present invention, cell aggregates are encapsulated in a conformal coating by passing them through a discontinuous liquid density gradient. The term "conformal coating" as used herein refers to a microcapsule coating that conforms to the shape of the coated product, closely following its contours. A suspension of cells and/or cell aggregates in an aqueous solution are introduced to the top or bottom of the density gradient (depending on the cells' density relative to the layers of the density gradient), sink or rise during centrifugation of the density gradient, are coated by a polymer solution, and are recovered from the opposite end of the density gradient conformally coated in a coating of precipitated biocompatible polymer.

The operation of the conformal coating process is now explained in detail below with reference to FIGS. 1 to 4.

Figure 1:
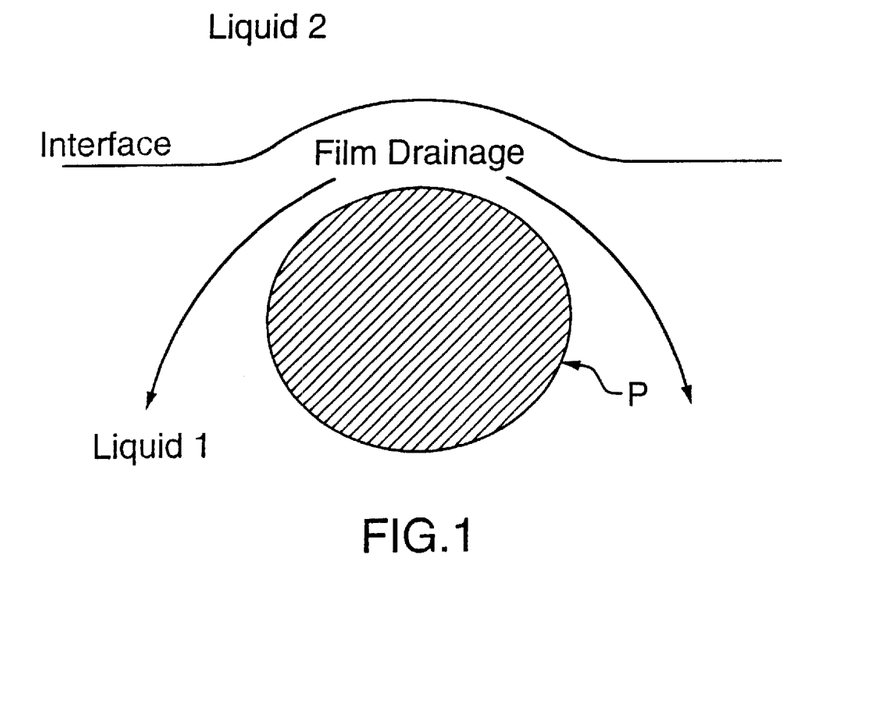
FIG. 1 is a schematic diagram illustrating film drainage of a first liquid from around a particle as the particle moves through the first liquid toward an interface between the first liquid and a second liquid.

FIG. 1 illustrates a particle P traversing a liquid (liquid 1) under the force of gravity, by sinking or rising. Particle P will either pass through or come to rest at an interface with another liquid (liquid 2) depending on the velocity of approaching particle P, the viscosity of the two liquids, their relative densities and the tension at the interface, as discussed by Hartland, *Journal of Colloid and Interface Science* 26(4):383–394 (1971), Hartland, *Chemical Engineering Science* 24: 987–995 (1969), Maru et al., *Chemical Engineering Science* 26:1615–1628 (1971), Stoos and Leal, *AIChE Journal* 35(2):196–212 (1987), and Geller et al., *J. Fluid Mech.* 169: 27–69 (1986).

As particle P nears the interface, FIG. 1 illustrates two processes occurring simultaneously. Firstly there is drainage of the thin film of liquid 1 between particle P and the interface (indicated by the arrows in FIG. 1), and secondly, deformation of the interface by the force of the approaching particle P.

If the viscous forces in the liquid around particle P (liquid 1) are large enough, the drainage of the film between particle P and the approaching interface is relatively slow and this will impede the particle's approach to the interface.

Figure 2:
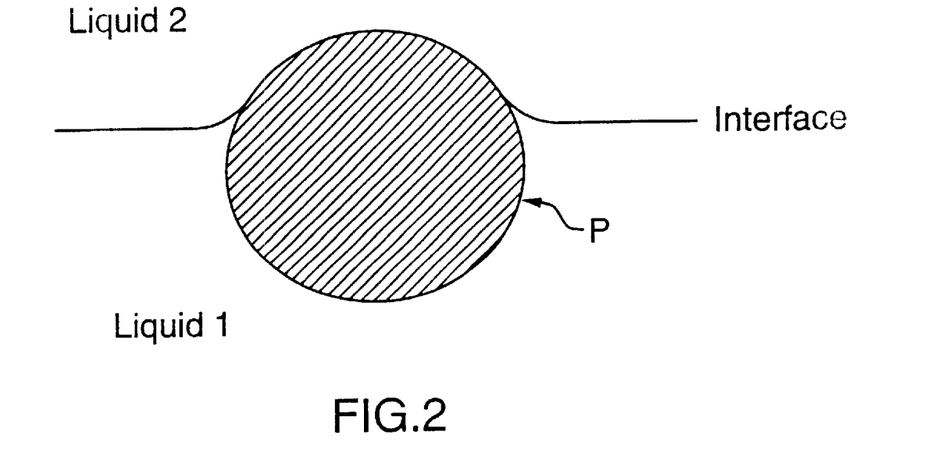
FIG. 2 is a schematic diagram showing the particle of FIG. 1 contacting the interface between the first and second liquids.

However, as shown in FIG. 2, if the interfacial tension is sufficient to prevent any large deformation of the interface, and/or if the viscous forces of the liquid above the interface (liquid 2) are large enough to resist deformation just above the interface, particle P will contact the interface. A similar outcome will occur, only more quickly, if the film drainage is faster, due to low viscosity of liquid 1, for example, and/or the velocity of particle P is higher. If particle P contacts the interface, as shown in FIG. 2, it will either pass through or rest in an equilibrium position at the interface, depending on the balance between interfacial and buoyancy forces.

Figure 3:
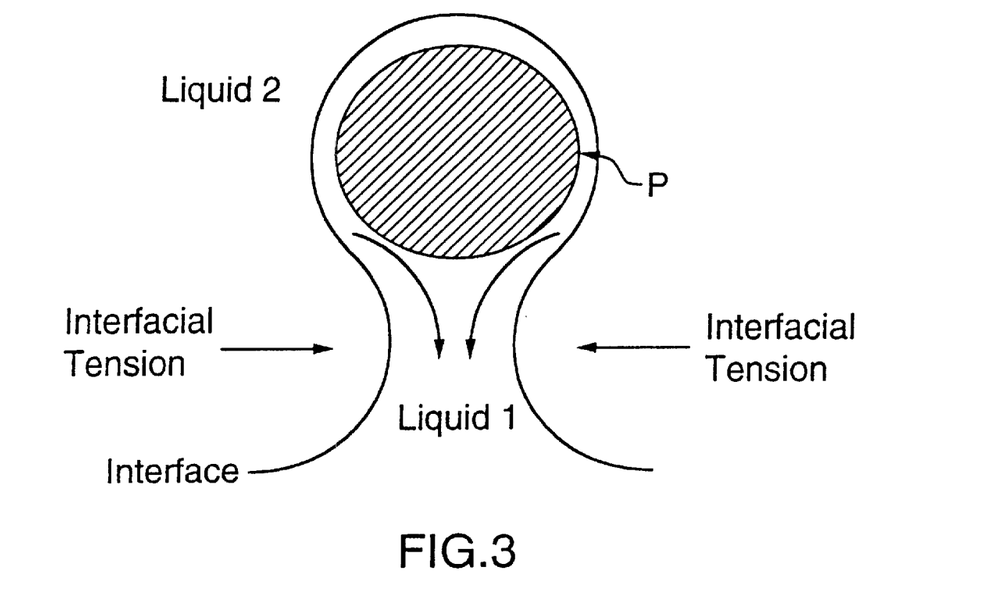
FIG. 3 is a schematic diagram showing the particle of FIG. 1 passing into the second liquid completely surrounded by a layer of the first liquid.

Another possible scenario, described by Maru et al. and Geller et al., and illustrated in FIG. 3, results in particle P passing into liquid 2 completely surrounded by a layer of liquid 1. The inventors have found that this can be used as a method for conformally coating cells and cell aggregates within a biocompatible polymer coating.

For encapsulation to occur, conditions for slow film drainage should be present, such as high viscosity of liquid 1, the liquid surrounding particle P, as in the case described above and show in FIG. 3. If the particle velocity is high enough, and the interfacial tension and the viscosity of liquid 2 are low enough, the momentum of particle P will cause the interface to deform normal to the interface. At large deformations, where particle P surrounded by entrained liquid 1 travels well past the line of the original interface, the interfacial forces (or tension, indicated by the two arrows in FIG. 3) and viscous drainage of the tail will pull the interface around the bottom of particle P, and cause it to become encapsulated in a coating of liquid 1. As long as film drainage is maintained throughout the deformation process, particle P will pass into liquid 2 without touching or passing through the interface between the two liquids, and will, in fact, remain surrounded by liquid 1. This is the mode in which the disclosed microencapsulation process operates and is shown in FIG. 3.

Figure 4:
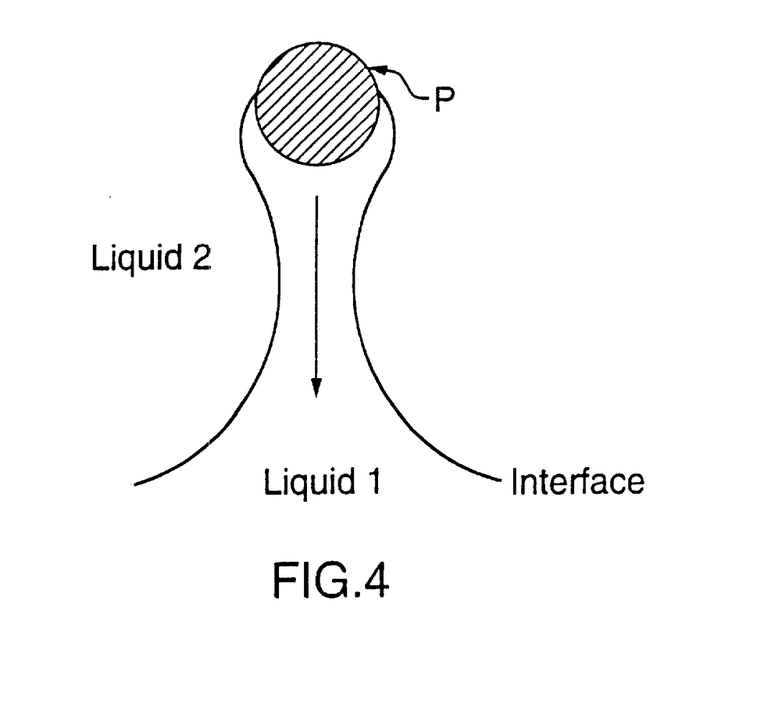
FIG. 4 is a schematic diagram showing how continued film drainage from around the particle of FIG. 3 will result in the particle contacting the interface and passing into the second liquid without being encapsulated in the first liquid.

In some cases, as shown in FIG. 4, film drainage from around particle P may continue via a long tail in the direction shown by the arrow. The tail may become unstable and break from interfacial tension forces, leaving particle P surrounded by a layer of liquid 1. However, if the tail persists, film drainage will continue until particle P touches the interface and passes directly into liquid 2 without being encapsulated in liquid 1.

Encapsulation of a particle or cell aggregate in a polymer by the process shown in FIG. 3 can be accomplished using a polymer solution as liquid 1. If the particle surrounded by the entrained polymer solution is subsequently passed into a solution that is a non-solvent for the polymer, a polymer coating will precipitate around the particle. Of course, the non-solvent solution cannot be liquid 2, since precipitation at the interface would occur and the process would be halted. Rather, additional layers are needed to preclude direct precipitation at the interface. Liquid 2 must therefore be an intermediate layer that will not precipitate the polymer, yet have the required properties for film drainage and large interfacial deformation.

Therefore, the conformal coating apparatus must have a density gradient comprising at least three layers, and consequently at least two interfaces. Preferably, the apparatus has five layers and four interfaces, with two solvent layers and two non-solvent layers arranged symmetrically about the polymer solution layer to accommodate cell aggregates having densities either less than or greater than the densities of the layers of the density gradient.

As the particle size decreases, the interfacial tension required becomes lower. Maru et al provide a relationship for the maximum interfacial tension above which particles of a certain size and density will rest in equilibrium at an interface. All four of the interfaces in the conformal coating apparatus must be below this critical interfacial tension; however, the interface where the polymer coating is entrained and coating occurs must have an even lower interfacial tension. An estimate of the required value for this interfacial tension from Leal et al, is less than $10^{-3}$ dynes/cm.

Some cell aggregates, such as pancreatic islets, cannot withstand large shear forces from excessive centrifugation. The interfacial tension should be very low when encapsulating these cell types. To achieve such low interfacial tensions, the solvent used in the polymer solution is preferably also used as one or both of the solvent layers, since solvent and a polymer solution in the same solvent will produce an interfacial tension approaching zero.

To adjust the properties of the solvent layer, a second polymer, different from the coating polymer of liquid 1 may preferably be dissolved in the solvent of liquid 2. The density, viscosity and the interfacial tension may then be adjusted by varying the concentration and molecular weight of the polymer in liquid 2. One important characteristic of this second polymer is that it should be soluble in the same solvent as the coating polymer. However, unlike the coating polymer, it is preferably also soluble in the non-solvent layers. This will ensure that the aggregate is coated with the coating polymer only. In addition to adding the second polymer to vary properties of the adjacent solvent layer, the presence of the second polymer also decreases the thermodynamic driving force for the mixing of these two similar layers. Extensive mixing of the layers would destroy the crucial coating interface. Similar aqueous multiphase systems are used extensively for biological separations as described by Albertsson, *Partition of Cell Particles and Macromolecules,* 3rd Ed. (John Wiley and Sons, 1986), which is hereby incorporated by reference.

Using an aqueous solution as the non-solvent to precipitate the polymeric coating provides a natural environment for the cells while precipitation occurs. Preferably, the cells are introduced into the system as an aqueous suspension. The aqueous solution in which the cell aggregates are suspended may form one of the non-solvent layers. This can be accomplished by placing another solution of the non-coating polymer in solvent, of greater concentration for a higher density, below the coating polymer layer, and then a final dense aqueous layer at the bottom of the gradient into which the cells can enter. This allows the cells to enter in an aqueous environment, pass briefly through a set of non-aqueous layers in which they are coated by interfacial deformation, and leave in an aqueous environment surrounded by a precipitated conformal coating. If the cell aggregates are of greater density than the density gradient layers and fall through the apparatus, the lower solvent layer will form the coating interface with the polymer layer. It is important that the polymer added to the solvent of this layer to increase its density be low in molecular weight, so that its viscosity remains much less than the coating polymer layer (see above for importance of viscosity). A density enhancer, such as metrizamide, can be added to the lower aqueous phase to produce a bottom aqueous layer of sufficient density.

In most known microencapsulation methods, the formation of droplets containing a suspension of cells is the underlying factor that determines the final dimensions of the microcapsules. In contrast, the dimensions of microcapsules produced according to the present invention depend directly on the dimensions of the cell aggregate being coated. Therefore, the encapsulation method of the present invention has greater potential to produce ultra-small microcapsules that conform to the shape of the cell aggregates and minimize the volume of the microcapsule.

In order for interfacial deformation and polymer entrainment around the cell aggregates to occur, there should be low resistance to deformation of the interface, produced by low interfacial tension and low liquid viscosity of the liquids adjacent to the entrained liquid, and slow film drainage around the cells as they approach the interface, produced by high viscosity of the entrained liquid. Intermediate layers of additional solvent solutions between the coating polymer solution and the aqueous layers prevent premature precipitation at the interfaces. Varying the polymer concentration and molecular weight of these intermediate layers changes the density, interfacial tension, and viscosity of the layers. Varying the centrifuge speed changes the velocity of the cell aggregate. These adjustments provide means of controlling the physical characteristics of the final coating.

Figure 5:
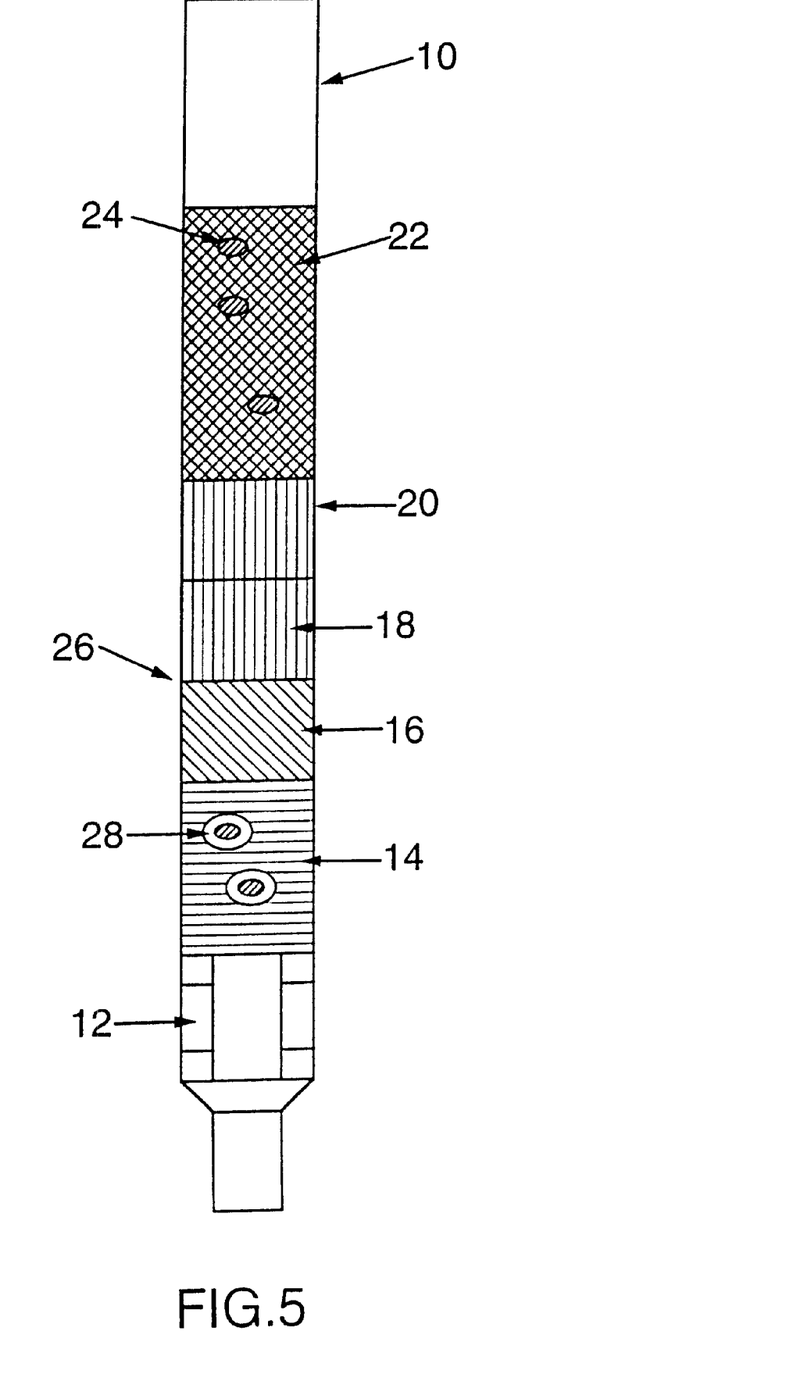
FIG. 5 is a side view of a coating chamber according to the present invention for use in conformal coating of HepG2 cell aggregates.

The density gradient is formed in a coating chamber. The term "coating chamber" as used herein refers to any vessel in which a density gradient can be formed, into or out of which a cell aggregate solution can be introduced or removed from the bottom layer after the density gradient has been formed, and which can be subjected to centrifugal force. For example, the coating chamber can be a centrifuge tube or a tube with one closable end, such as a column or a syringe with a stopcock (FIG. 5). Two three-way stopcocks in series at the bottom of a syringe adds further complexity and permits addition and removal of the bottom layer of the density gradient without disturbing the above layers. The liquids forming the layers in the density gradient are chosen for their physical and chemical properties. Preferred properties of each layer of the density gradient are described below.

(a) Lower Non-solvent Layer (Bottom Layer)

The bottom layer is a small volume of a non-solvent solution and has the highest density of any layer. The aqueous solution used to deliver cells or precipitate the polymer may preferably include a buffering compound such as sodium phosphate, sodium bicarbonate, N-2-hydroxyethyl piperazine-N'-2-ethanesulfonic acid (HEPES), BFS, MOPS, TAPSO, TES, TRIS, MES or TRICINE depending on the sensitivity of the cells to these compounds. Also, the aqueous solution may contain a compound for maintaining isotonicity such as sodium chloride, glycerol or glucose. Preferred are isotonic cell buffers such as PBS (phosphate buffered saline) or a medium that maintains the viability of the encapsulated cells. More preferred are standard cell media such as αMEM (minimum essential medium) or RPMI 1640 to be used for delivering the cells to be encapsulated.

The density of the bottom layer may preferably be increased by dissolving therein any suitable compound, preferably inert and non-injurious to the cells to be coated. Preferred compounds are water-soluble and of high molecular weight, so that the isotonic environment of the cells is not greatly compromised. Since the polymer solvent of the system and the polymers used in the solvent layers around the polymer layer are all water soluble, there will be a tendency for the layers to mix, especially with the passage of particles through the various interfaces. It is important, therefore, that the density enhancer does not lower the interfacial tension to a point where layer mixing occurs. A higher molecular weight density enhancer will decrease layer mixing by increasing the viscosity. When this bottom layer is the precipitation layer (cell-sinking system), the isotonic buffer plus density enhancer should maintain the viability of the cells and promote precipitation of the polymeric wall of the microcapsule. A particularly preferred example of such a bottom layer is a 30% w/v metrizamide (Sigma Chemicals) solution in PBS, with a specific gravity of 1.16 g/mL, or a 70% w/w glycerol (Sigma Chemicals) solution, with a specific gravity of 1.18 g/ml in PBS.

(b) Dense Lower Solvent Layer (Second Layer)

A dense solvent layer separates the first (lower non-solvent) and third (polymer solution) layers, since contact between these first and third layers would cause precipitation of the polymer in the third layer. Therefore, in a sinking cell aggregate system, this lower solvent layer also prevents premature precipitation of the incipient polymer coat.

The solvent in this lower solvent layer can preferably be any liquid in which the chosen polymer can dissolve. Preferred solvents include PEG, methoxy PEG, methoxy PEG acetate, PEG diacetate, triethylene glycol (TEG), polypropylene glycol, acetone, benzyl alcohol, butanediol, butanone, cyclohexyl pyrrolidone, dibutyl phthalate, dimethyl acetamide, dimethyl sulphoxide, dioxane, ethanol, ethylene glycol, glycerol, hexadecane, hexanediol, methyl pyrrolidone, methoxy benzyl alcohol, octanediol, pentanediol, phenyl ethanol, phenyl butanol, propanediol, sulfolane, tetraglyme, toluene, benzene, xylene, methylene chloride, chloroform, chlorobenzene, isobutanol, cyclohexanol, methyl ethyl ketone, cylclohexanone, acetic acid, isobutyric acid, ethyl acetete, cyclohexyl acetate, carbon tetrachloride, nitroethane, tetralin, glycol ether and tetrahydrofuran. It is to be understood that the number of possible solvents is virtually inexhaustible, with the specific choice of solvent depending on the particular polymer composition and on the application.

For microencapsulation of cells, more preferred solvents are those which are non-toxic to the cells or at least which the cells can tolerate for the brief period to which they are exposed to the solvent. Preferably, the solvent is the same as the polymer solvent in the coating polymer solution layer.

Particularly preferred solvent layers for microencapsulation of cells include polyethylene glycol (PEG) and TEG.

The density of the lower solvent layer may preferably be increased by adding to it a different, non-coating polymer. In a cell-sinking system, the concentration of the second, non-coating polymer in this layer, and the volume of the layer, determine the quality, shape, and thickness of the coating. The molecular weight of the polymer added to the solvent should be low to maintain a low viscosity.

A particularly preferred example of the lower solvent layer comprises a 30% w/w solution of polyvinylpyrrolidone (PVP-M.W. 10,000) in polyethylene 200 (PEG200) with a specific gravity of approximately 1.15 g/mL and a volume of 0.1 mL in a 1 mL Tuberculin Syringe.

(e) Coating Polymer Layer (Third Layer)

The third layer is a solution of the polymer that will coat the cells. The polymer is preferably any biocompatible polymer that precipitates in an aqueous environment. In the case of microcapsules, the polymer must also be semipermeable after fully precipitating, this semipermeability not being necessary in the case of microspheres. Polymers used in the method of the present invention include but are not limited to polymers having angiogenic properties. Preferably, polymers used in the method of the present invention are substantially insoluble in water and aqueous salt solutions.

Preferred polymers for use in the method of the present invention are those listed above in the discussion of the Angiogenic Material. Unsuitable polymers are those like polyethylene oxide, polylysine, alginate and other polysaccharides, which are water soluble, or polyethylene or polypropylene, which are difficult to dissolve to form a solution at moderate temperatures. Since the preparation of copolymers of a wide variety of compositions and membrane precipitation techniques allows one skilled in the art to prepare polymers with a range of solubilities and permeabilities, the range of suitable polymers is almost inexhaustible.

More preferably, the polymer is polyacrylate, and most preferably hydroxyethyl methacrylate-methyl methacrylate (HEMA-MMA) or hydroxyethyl methacrylate-methyl methacrylate-methacrylic acid (HEMA-MMA-MAA).

The solvent in which the coating polymer is dissolved is selected from those discussed above in the context of the lower solvent layer.

A coating of the coating polymer solution becomes entrained around the cell aggregate at the interface between the coating polymer layer and the upper solvent layer in a rising cell system, and the lower solvent layer in a sinking cell system. The polymer concentration and density of this layer are adjusted to obtain conformal coats with desired characteristics.

The polymer in solution may preferably be at any concentration that results in microcapsule formation. For microcapsule formation, factors to be considered in choosing a polymer concentration include the viscosity and density of the polymer solution. The viscosity is determined by both the concentration and molecular weight of the polymer used in the polymer solution. These characteristics must be coordinated with the characteristics of the other solutions used in microcapsule formation. This coordination of characteristics is described fully below.

Preferably, the concentration of polymer is chosen to result in a viscosity that is high enough to allow the polymer solution to become entrained around a cell aggregate but low enough to allow the coated cell aggregate to pass through the polymer solution fast enough prior to any toxic effects from the solvent. Preferably, the polymer solution contains between about 5% and about 20% polymer by weight.

A particularly preferred example of the coating polymer solution is a 10% solution of HEMA-MMA in PEG200 with a specific gravity of 1.135 g/mL and a volume of about 0.1 mL in a 1 mL Tuberculin Syringe. The polymer solution can also preferably contain a vascularization compound as described earlier, such as methacrylic acid.

(b) Upper Solvent Layer (Fourth Layer)

The upper solvent layer has a similar role as the lower solvent layer and may have the composition discussed above with reference to the lower solvent layer, with the exception that it must have a density greater than that of the upper non-solvent layer and less than the other layers. In a rising cell system, it prevents premature precipitation of the incipient polymer coat and preferably contains a polymer different from the coating polymer. The concentration of preferred non-coating polymer in this layer, and the volume of the layer, determine the quality, shape, and thickness of the coating in the rising cell system.

For example, pure PEG 200 is preferred for this layer for both the rising or falling cell scenario. For the rising cell system, coating characteristics may preferably be varied by the addition of PVP, polyacrylic acid (e.g., PAA of molecular weight 90,000 daltons) or Dow Corning DC193 surfactant, a siloxane glycol copolymer.

(e) Upper Non-solvent Layer (Fifth Layer)

The properties and purpose of this non-solvent layer are similar to those of the lower non-solvent layer. Therefore, this layer may have the composition discussed above with reference to the bottom layer, with the exception that it must be less dense than the other layers.

This top layer is where the polymer coating precipitates onto the cell aggregates for a rising cell system. For rising cell systems, the precipitation solution in this layer may preferably be any isotonic buffer that maintains the viability of the encapsulated cells and promotes precipitation of the polymeric wall of the microcapsule. A preferred solution for the upper non-solvent layer is an isotonic cell buffer such as PBS. The density of this solution may be increased to be greater than that of the coated cells by dissolving therein any suitable compound, preferably inert and non-injurious to the cells to be coated. Any water-soluble, high molecular weight compound that does not cause layer mixing by decreasing the interfacial tension, or increases layer stability by increasing the non-solvent viscosity slightly are suitable.

The density of this layer must be greater than that of the coated cells so that the rising cell aggregates (having a specific gravity close to that of water) will pass into the layer and to the top of the layer where they can be easily removed.

A preferred example of the upper non-solvent layer is an aqueous solution of 30% w/w glycerol with a density of approximately 1.09 g/mL.

For a sinking cell system, the upper non-solvent layer is the layer into which cell aggregates are fed into the apparatus, and it is sufficient that it be composed of pure PBS or cell medium without any density enhancement.

The density and viscosity of the upper and lower_solvent layers, the viscosity of the coating polymer layer, and the interfacial tension between the coating polymer layer and the upper solvent layer or the lower solvent layer are preferably adjusted to vary the coat thickness and to optimize the conformal coating process when using different polymers or cell aggregates. The coat thickness can vary from greater than 0 $\mu$m to about 80 $\mu$m, or more generally, the total diameter of the coated cell aggregate is from slightly greater than 1 to about 1.6 times the diameter of the cell aggregate before coating. Preferably, the interfacial tension between the polymer solution layer and the upper solvent layer (in the case of rising cell systems) is minimized by using the same solvent in both layers. For example, the coat thickness around a floating cell aggregate will be decreased by decreasing the density of the upper solvent layer and/or increasing its viscosity. This can be accomplished by adding DC193 (Dow Corning) to PEG 200 for the upper solvent layer. Conversely, to decrease the size of a sinking cell aggregate, the density of the lower (dense) solvent layer must be decreased so that it approaches the density of the polymer layer and/or its viscosity increased. This can be accomplished by using a slightly less concentrated, but of higher molecular weight, PVP solution in PEG200 (25% as opposed to 30%) for the lower solvent layer.

The densities of the layers must decrease from the bottom to the top of the coating chamber. The densities of the layers are adjusted by adding appropriate amounts of solutes of different density than the liquid in which it is dissolved. For example, the density of the lower non-solvent layer can be increased by adding a density enhancing solute such as metrizamide (Sigma). The density of the dense solvent layer can be increased by adding polyvinylpyrrolidone (PVP). The density of the upper non-solvent layer can be increased by adding a density enhancing solute such as glycerol (Sigma). Suitable density increasing solutes must be able to increase density without increasing viscosity too much, be non-toxic, not able to dissolve the coating polymer, be soluble in water (if cells are used), have a low surface activity so that mixing between adjacent layers is minimized, and be of relatively high molecular weight to minimize osmotic pressure on the cells. Examples are sucrose, Percoll, Ficoll, Dextran, metrizamide, glycerol and water-soluble polymers such as polyvinyl alcohol, PAA and PVP.

The coating chamber can be any vessel in which a density gradient can be formed, into which a cell aggregate solution can be introduced after or during the formation of the density gradient, and which can be subjected to centrifugal force. For example, a 1 mL Tuberculin Syringe (Becton Dickinson) can be used as the coating chamber. To close the bottom of the syringe, the rubber plunger is cut from the stem and pushed to the bottom of the syringe as a plug. This is the simplest version of the coating chamber.

Cell aggregates that have a specific gravity greater than 1.18 g/ml (a sinking cell system) are preferably conformally coated by forming a density gradient in a coating chamber, introducing a cell aggregate suspension to the top of the coating chamber as the upper non-solvent layer, centrifuging the coating chamber, and collecting conformally coated cell aggregates from the bottom of the coating chamber.

The liquids of the density gradient are layered into the conformal coating apparatus carefully and slowly to prevent mixing. For example, 1 mL syringes with blunt 15 gauge needles are adequate for layering solutions directly on top of previous layers. The solutions are layered in the following order: lower non-solvent solution (first layer), dense solvent solution (second layer), polymer solution (third layer), upper solvent solution (fourth layer), and upper non-solvent solution (fifth layer).

For the sinking cell system the cell aggregates are introduced into the top aqueous layer. The cell aggregates immediately begin to sink since they have a higher density than the density gradient solutions. After introducing the cell aggregates to the coating chamber, the coating chamber is subjected to centrifugation. The effective G-force of the centrifugation is important for determining the velocity of the cell aggregates through the density gradient layers and through the coating interface. A moderate effective G-force of between 800 and 1000 g's is sufficient. The greater the density difference between the density gradient solutions and the particles to be coated or the higher the immiscibility between the layers, the lower the effective G-force can be. After centrifugation, conformally coated cell aggregates are retrieved from the bottom layer by cutting the syringe at the lower non-solvent layer. This exposes the coated cells and allows them to be removed easily by pipette into PBS for further precipitation and use.

The disclosed conformally coated cell aggregates have several desirable characteristics. The polymeric coat is thin, with the thickness varying from greater than 0 $\mu$m to 80 $\mu$m, depending on the composition of the solutions in the density gradient layers. The polymeric coat shrinks after the solvent is removed. The thickness of the polymeric coat after shrinkage is referred to as the final thickness. Preferred conformally coated cell aggregates have a final polymeric membrane thicknesses of less than 10 $\mu$m. Since the process produces a coating that conforms to, and then "shrink wraps" around, the cell aggregate, the resulting microcapsules have essentially the same volume as the original uncoated cell aggregates.

FIG. 5 illustrates a preferred coating chamber for conformal coating of HepG2 cell aggregates comprising a 1 mL tuberculin syringe 10 plugged at its bottom by rubber plunger 12 which has been removed from the stem of the plunger of the syringe 10. The five liquid layers of the density gradient are, from bottom to top: a lower non-solvent layer 14 comprising a 60% (w/w) aqueous glycerol solution; a lower solvent layer 16 comprising a 30% (w/w) solution of PVP in PEG200; a polymer solution layer 18 comprising a 15% (w/w) solution of HEMA-MMA (coating polymer) in PEG 200; an upper solvent layer 20 comprising pure PEG200; and an upper non-solvent layer 22 comprising cell culture medium. As shown in FIG. 5, HepG2 cell aggregates 24 are introduced at the top of the density gradient and become coated with the polymer solution 18 at the coating interface 26 between polymer solution layer 18 and lower solvent layer 16. The conformal coating of HEMA-MMA then precipitates on the cell aggregates 24 in the lower non-solvent layer 14 and the conformally coated cell aggregates 28 are recovered from the lower non-solvent layer 14 at the bottom of the density gradient, for example, by cutting the syringe 10 at the lower non-solvent layer 14 and withdrawing the coated cell aggregates 28.

5. Formation of Microspheres

To produce small coated bubbles, or microspheres, a similar process to the above can be followed with minor modifications. Producing microspheres is simplified since bubble density is much less than the density of the gradient and the added complications of maintaining cell viability are absent.

The simplest gradient for coating bubbles consist of a polymer solution bottom layer in which bubbles are suspended, an upper solvent layer and a top non-solvent layer. Coated bubbles can be removed from the upper layer for additional precipitation and use.

Bubbles are suspended in the polymer layer by mixing polymer solution, for example, using the highest setting on a vortex mixer. This produces a suspension of relatively small bubbles (50–200 $\mu$m) that can be coated within 10 minutes without centrifuging the apparatus (1 ml syringe, as before) due to the low density of air bubbles. To produce a narrower distribution of bubble sizes, or to produce smaller bubbles, the suspension can be drawn into a syringe, which when capped can be used to pull a vacuum on the bubble suspension. Larger bubbles will quickly rise and coalesce leaving only the smaller bubbles in suspension. Such small bubbles may require centrifugation for successful coating; however, the speed and time required is much less than for cell aggregates or other particles with densities that are closer to the densities of the gradient.

In one preferred aspect, bubbles with initial coating thicknesses of 20 to 40 $\mu$m can be produced using 15% HEMA-MMA in PEG200 as the bottom layer, pure PEG200 as the solvent layer and distilled water as the non-solvent layer.

Due to the high viscosity of the polymer solution, it can be easier to produce an aqueous suspension of small bubbles. In this case the arrangement described for coating cell aggregates, having a density gradient comprising five layers, is preferably maintained. For example, a fine suspension of bubbles can be produced in a 60% aqueous glycerol solution with 10% Ficoll added to increase the viscosity slightly so that the bubbles remain in suspension. If this aqueous suspension is the bottom layer of a density gradient consisting of (bottom to top) 30% PVP in PEG200, 15% HEMA-MMA in PEG200, pure PEG200 and finally, distilled water, a large number of ultra small coated bubbles can be obtained from the top water layer.

Although the preferred forms of the process for forming microspheres discussed above utilize aqueous non-solvent layers, it is to be understood that the non-solvent layers need not be aqueous. However, if aqueous non-solvent layers are used, the aqueous solution need not be isotonic or buffered.

Because toxicity is not a concern during the production of microspheres, a wider range of solvents may be used in the solvent and polymer solution layers than in the case of microcapsule production. However, since bubbles rise, the solvent layer and polymer solution layer must be more dense than the non-solvent layer.

The invention is further illustrated by the following examples.

EXAMPLES

Materials and Assays

Cells and Cell Culture

HepG2 cells were obtained from American Type Culture Collection (ATCC: Rockville, Md.). The cells were routinely maintained in α-MEM, an isotonic mixture of salts and nutrients used to maintain cell viability for example during in vitro cell culture, supplemented with 100 U/mL penicillin, 100 $\mu$g/mL streptomycin and 10% fetal bovine serum (FBS: Sigma Chemicals, St. Louis, Mo.) using conventional cell culture techniques.

Conformal Coating Microencapsulation

Conformal Coating Chamber

A 1 mL Tuberculin Syringe (Beckton Dickinson) plugged at the bottom with its plunger (stem removed) was used as the conformal coating apparatus and is shown in FIG. 5.

Preparation of Density Gradient

The liquids of the density gradient were layered into the pre-loaded coating chamber carefully and slowly to preventing mixing. The following solutions were layered in order:

Non-solvent layer (first layer from the bottom): a volume of 0.1 mL to 0.2 mL of 60% w/w glycerol(Sigma Chemicals) in PBS with a specific gravity of 1.18 g/mL.

Dense solvent layer (second layer): a 30% w/w solution of polyvinyl pyrrolidone (PVP) (M.W. 10,000) (Aldrich) in PEG200 (BDH Chemicals) with a specific gravity of 1.15 g/mL and a volume of 0.05 mL.

Polymer solution layer (third layer): a 15% solution of HEMA-MMA in PEG200 with a specific gravity of 1.142 g/mL and a volume of 0.05 mL.

Upper solvent layer (fourth layer): pure PEG200 with a volume of 0.05 ml.

Upper non-solvent layer (fifth layer): an aqueous solution of HepG2 cells in medium with a density of approximately 1.00 g/ml.

Centrifugation and Coating

After adding the top layer consisting of aqueous cell suspension, the cell aggregates began to sink. The apparatus was immediately placed in a centrifuge (IEC, "Clinical" benchtop bowl centrifuge) for 5 minutes at 3000 RPM (1000 g). After centrifugation, conformally coated cell aggregates were retrieved from the bottom layer by capping the top of the syringe with parafilm and cutting the syringe to expose the cells in the bottom layer. Cells were then removed from the bottom layer with a pipette and placed in PBS solution for further precipitation and use.

Vascularization of Implanted Microspheres

Polymers

Hydroxyethyl methacrylate-methyl methacrylate (HEMA-MMA; 75% HEMA) was prepared by solution polymerization using azobisisobutyronitrile as an initiator (0.1 mol %), as described previously. Hydroxyethyl methacrylate-butyl methacrylate (HEMA-BMA; 85 mole % HEMA) and hydroxyethyl methacrylate-butyl methacrylate-methacrylic acid (HEMA-BMA-co-MAA; mole ratio 68:30:2) were prepared in a similar fashion by solution polymerization. Polymethyl methacrylate-methacrylic acid (PMMA-MAA; 10% MAA) (lot # 53816) and polymethyl methacrylate (PMMA; MW 100,000, micron size 50–150) (lot # 85383) were both from Polysciences, Inc., (Warrington, Pa.).

Microsphere Formation

"Small diameter" microspheres (~400 $\mu$m in diameter) were prepared using a submerged nozzle-liquid jet extrusion process [Uludag et al, *Biotech. Bioeng.* Vol. 44, 1199–1204 (1994)] using 10% HEMA-MMA in triethylene glycol (TEG; MW 150, Aldrich), 10% (w/v) HEMA-BMA in polyethylene glycol 200 (PEG-200; BDH Chemicals, Toronto, Ontario), 10% (w/v) HEMA-BMA-MAA in PEG-200, 10% (w/v) PMMA-MAA in dimethyl formamide (DMF), or 25% (w/v) PMMA in DMF. The core solution was 15% (w/v) Ficoll-400 (Sigma, St. Louis, Mo.) in phosphate buffered saline (PBS; pH 7.4, in g/L: 8.7 NaCl, 6.1 $Na_2HPO_4$, 1.1 $NaH_2PO_4$ ) or nothing. Microspheres were maintained in PBS for 1 week prior to implantation.

"Large diameter" hydroxyethyl methacrylate-methyl methacrylate [HEMA-MMA; 75 (mole %) HEMA] microspheres (~750 $\mu$m in diameter) were prepared using the submerged jet coaxial extrusion interfacial precipitation process [Crooks et al., 1990]. Core solutions consisted of a 1:1 (v/v) mixture of complete tissue culture medium and Matrigel® (Collaborative Research, Bedford, Mass.) or 20% (w/v) Ficoll-400 (Sigma, St. Louis, Mo.) in complete tissue culture medium (αMEM+FBS) or 20% Ficoll but without FBS in the tissue culture medium.

Animals

Male Wistar rats (175–200 g) (Charles River Canada Inc., St. Constant Quebec, Canada) were used as the recipients for polyacrylate microspheres. Animals were kept under conditions of controlled temperature (25 C.) and 12 h light-dark schedule throughout the microsphere implantation duration. Food and water were available ad lib.

Implantation

Microspheres were washed with PBS (3 times over 10 min.) and then implanted into recipient rats intraperitoneally (IP), intramuscularly (IM), or in an intramuscular/omental pouch (IM/OM); 2–5 animals per sample type as indicated in the Tables. Rats were anaesthetized with Ethrane (4–5% (v/v) in air), the ventral area shaved and wiped with an isopropanol solution (70%, Regal Pharmaceuticals, Burlington, Ontario, Canada). For IP implants, a small incision was made (~2 cm long, 2 cm below sternum) and 200 small diameter or 50 large diameter microspheres, suspended in PBS, were placed in the vicinity of the stomach using a sterile custom made glass pasteur pipette with a flame-polished tip. For IM implants, 20 large diameter microspheres were placed into two pockets formed in the abdominal muscle on either side of the midline. For IM/OM implants, 20 microspheres were placed into an abdominal intramuscular pouch into which the omentum was pulled through a hole formed at the end of the IM pocket lateral to the midline which was secured with 6 'o' sutures. The muscle layer was sutured with 6 'o' silk sutures, the skin layer sutured with 4 'o' silk sutures and the incision coated with collodion. Microsphere implantation duration was 2 weeks.

Microsphere Recovery

Two weeks after implantation surgery, the rats were anaesthetized with an injection of Atravet acepromazine maleate (0.1 ml/100 g; 1 mg/mL, Ayerst Laboratories, Montréal, Québec) and Rogarsetic ketamine hydrochloride (0.1 mg/100 g; 115.4 mg/mL, Vetrepharm Canada, London, Ontario). The ventral area was shaved and wiped with isopropanol solution. In a sterile laminar flow hood, the peritoneal cavity was exposed. For IP implants, microspheres were recovered by gently examining the entire peritoneal cavity removing them as attached to the omentum or as attached to the suture line. Additional spheres were recovered freely floating in the peritoneal cavity but these are not described further. Recovered microspheres and associated tissue were washed with PBS and then fixed [3.5% (v/v) glutaraldehyde (EM grade; Polysciences, Warrington, Pa.); containing 2% (w/v) tannic acid in 0.1 M Sorenson's phosphate buffer (P-buffer)]. IM and IM/OM implants were recovered within the intact tissue, washed with PBS and fixed.

Light Microscopy

Tissue samples containing capsules or beads were prepared for light microscopy. Fixed samples were washed with PBS (2×15 min.) and cryoprotected with 30% (w/v) sucrose in PBS at 4 C overnight. Samples were then frozen embedded in OCT compound (Miles Inc., Diagnostics Division, Elkhart, Ind.) within a plastic mold (Miles Inc., Diagnostics Division, Elkhart Ind.). Serial cryostat sections (8–10 $\mu$m in thickness), cut at −20 C, were cleared of OCT in water and then stained with either aqueous toluidine blue (0.1% (w/v) in distilled water, BDH Chemicals, Toronto, Ontario), Masson trichrome (Sigma, St. Louis, Mo.) or Harris haemotoxylin and alcoholic eosin (Sigma, St. Louis, Mo.).

Histological sections were examined using light microscopy and the number of blood vessels within 250 $\mu$m of the microsphere in the associated tissue reaction and surrounding tissue were determined. Blood vessels were identified based on the presence of intact endothelium with or without red blood cells. Immune and inflammatory cells were identified based on morphological criteria and the percent make up of each cell type to the cellular profile of the tissue reaction was assessed.

Vascularization of Implanted Microspheres

Histological assessment of the extent of vascularization of microspheres made with different polymers are shown in Table I. Microspheres made with polymer containing methacrylic acid (MMA:MAA=90:10) showed a significantly greater number of blood vessels nearer the polymer surface, with limited number of inflammatory cells such as macrophages or foreign body giant cells. The HEMA-MMA polymer also had a good vascularization response in some cases (Table II), presumably because of the traces of methacrylic acid that are in this polymer and which cannot be removed by conventional purification of the starting monomers. The addition of MAA at a molar concentration of 2% (to the HEMA-BMA monomer mixture) did not appear to be sufficient to increase the vascularization of the tissue response. Too little of the MAA was incorporated into the polymer to have an effect; the "2% MAA" was used on the monomer composition, not the final copolymer composition. Sterile, pyrogen free microspheres (10–50 $\mu$m in diameter) of poly HEMA-MMA, 75% HEMA, were made without cells and biological components by a method published elsewhere (Uludag et al., Viability and protein secretion from human hepatoma (HepG2) cells encapsulated in 400 $\mu$m polyacrylate microcapsules by submerged nozzle-liquid jet extrusion, Biotech. Bioeng. Vol. 44, 1199–1204 (1994)). HEMA-MMA contains traces of methacrylic acid, a vascularization compound. About 2,000 were infused into a coronary artery of an 18 kg pig, contralateral to a stenotic coronary artery. The latter was created four weeks previously by insertion of a metal coil by balloon dilation using the model of Schwartz et al. (Circ., Vol. 82, 2190–2200, 1990). There was no gross evidence of abnormalities (e.g. by intraoperative contrast echocardiography or electrocardiogram) indicating that the microspheres did not create clinically significant ischemia themselves.

TABLE I

Degree of vascularization of polyacrylate microsphere implantations: effect of polymer composition (two weeks after implantation)

| Polymer | Implantation Site | Core | Overall Degree of Vascularization |
|---|---|---|---|
| HEMA-MMA (75-25) | IP attached (suture line) | PBS + 15% (w/v) Ficoll | 2 |
|  | IP attached (omentum) |  | 1 |
| HEMA-BMA (85-15) | IP attached (omentum) | PBS + 15% (w/v) Ficoll | 1 |
| MMA-MAA (90-10) | IP attached (suture line) | none | 4 |

TABLE I-continued

Degree of vascularization of polyacrylate microsphere implantations: effect of polymer composition
(two weeks after implantation)

| Polymer | Implantation Site | Core | Overall Degree of Vascularization |
|---|---|---|---|
| | IP attached (omentum) | | 4 |
| HEMA-BMA-MAA (68-30-02) | IP attached (suture line) | none | 2 |
| | IP attached (omentum) | none | 1 |

(Capsules incubated in PBS after preparation)
Scoring Scale
1 = 0–15 blood vessels within 250 $\mu$m of polymer
2 = 0–30 blood vessels within 250 $\mu$m of polymer
3 = 0–85 blood vessels within 250 $\mu$m of polymer
4 = 0–116 blood vessels within 250 $\mu$m of polymer Table II Degree of vascularization of "large diameter" HEMA-MMA microsphere (no cells) implantations: effect of implantation site and capsule contents
(two weeks after implantation)

| Implantation Site | Core | Degree of Vascularization |
|---|---|---|
| IM | α-MEM + FBS/Matrigel | 3 |
| IM/OM | α-MEM + FBS/Matrigel | 2 |
| IM/OM | α-MEM + FBS/20% Ficoll | 2 |
| IP attached | α-MEM/20% Ficoll | 1 |
| IP attached | α-MEM + FBS/Matrigel | 3 |
| IP attached | α-MEM + FBS/20% Ficoll | 1 |
| IP attached | none | 2 |

(capsules incubated in PBS after preparation)
Scoring Scale
1 = 0–15 blood vessels within 250 $\mu$m of polymer
2 = 0–30 blood vessels within 250 $\mu$m of polymer
3 = 0–85 blood vessels within 250 $\mu$m of polymer Those skilled in the art will recognize, or be able to ascertain using no more than routine experimentation, many equivalents to the specific embodiments described herein. Such equivalents are intended to be encompassed by the following claims.

What is claimed is:

1. A method for increasing blood flow in the vicinity of a wound consisting of bed sores, venous ulcers, diabetic ulcers or burn wounds comprising:
   applying micro spheres consisting of an angiogenic material to the surface of the wound,
   said angiogenic material consisting of a biocompatible polymer and a vascularizing compound consisting of polymerizable compounds capable of forming anions and which promote the growth of blood vessels, which, when implanted in animal tissue, said angiogenic material promotes generation of blood vessels in its immediate vicinity and induces minimal or no fibrous capsule formation.

2. A method as claimed in claim 1 further comprising, before applying said microspheres to the surface of said wound, incorporating said microspheres into a wound care product consisting of wet dressings, dry dressings, occlusive dressings, non-occlusive dressings or wound pastes.

3. A method as claimed in claim 2, wherein said vascularizing compound consists of a polymerizable compound containing an ionizable group consisting of sulfates, sulfonic acid groups or carboxyl groups.

4. A method as claimed in claim 2, wherein said vascularizing compound consists of acrylic acid, methacrylic acid, crotonic acid, itaconic acid, vinylsulfonic acid or vinylacetic acid.

5. A method as claimed in claim 2, wherein said biocompatible polymer consists of polyacrylates.

6. A method as claimed in claim 2, wherein said vascularizing compound consists of methacrylic acid which is incorporated into the biocompatible polymer at the time of polymerization.

7. A method as claimed in claim 1, wherein said vascularizing compound consists of a polymerizable compound containing an ionizable group consisting of sulfates, sulfonic acid groups or carboxyl groups.

8. A method as claimed in claim 1, wherein said vascularizing compound consists of acrylic acid, methacrylic acid, crotonic acid, itaconic acid, vinylsulfonic acid or vinylacetic acid.

9. A method as claimed in claim 1, wherein said biocompatible polymer consists of polyacrylates.

10. A method as claimed in claim 1, wherein said vascularizing compound consists of methacrylic acid which is incorporated into the biocompatible polymer at the time of polymerization.

11. A method for increasing blood flow to transplanted cadaverous gum tissue comprising:
    positioning microspheres consisting of an angiogenic material between the transplanted tissue and a host tissue along a suture line,
    said angiogenic material consisting of a biocompatible polymer and a vascularizing compound consisting of polymerizable compounds capable of forming anions and which promote the growth of blood vessels, which, when implanted in animal tissue, said angiogenic material promotes generation of blood vessels in its immediate vicinity and induces minimal or no fibrous capsule formation.

12. A method as claimed in claim 11, wherein said vascularizing compound consists of a polymerizable compound containing an ionizable group consisting of sulfates, sulfonic acid groups or carboxyl groups.

13. A method as claimed in claim 11, wherein said vascularizing compound consists of acrylic acid, methacrylic acid, crotonic acid, itaconic acid, vinylsulfonic acid or vinylacetic acid.

14. A method as claimed in claim 11, wherein said biocompatible polymer consists of polyacrylates.

15. A method as claimed in claim 11, wherein said vascularizing compound consists of methacrylic acid which is incorporated into the biocompatible polymer at the time of polymerization.

16. A method of increasing blood flow in the vicinity of a wound consisting of bed sores, venous ulcers, diabetic ulcers or burn wounds comprising:
    applying an angiogenic material to the surface of the wound,
    said angiogenic material consisting of a biocompatible polymer and a vascularizing compound consisting of polymerizable compounds capable of forming anions and which promote the growth of blood vessels, which, when implanted in animal tissue, said angiogenic material promotes generation of blood vessels in its immediate vicinity and induces minimal or no fibrous capsule formation.

17. A method as claimed in claim 16, wherein said vascularizing compound consists of a polymerizable compound containing an ionizable group consisting of sulfates, sulfonic acid groups or carboxyl groups.

18. A method as claimed in claim 16, wherein said vascularizing compound consists of acrylic acid, methacrylic acid, crotonic acid, itaconic acid, vinylsulfonic acid or vinylacetic acid.

19. A method as claimed in claim 16, wherein said biocompatible polymer consists of polyacrylates.

20. A method as claimed in claim 16, wherein said vascularizing compound consists of methacrylic acid which is incorporated into the biocamptible polymer at the time of polymerization.

21. A method as claimed in claim 16, further comprising, before applying said angiogenic material to the surface of said wound, incorporating said angiogenic material into a wound care product consisting of wet dressings, dry dressings, occlusive dressings, non-occlusive dressings or wound pastes.

22. A method as claimed in claim 21, wherein said vascularizing compound consists of a polymerizable compound containing an ionizable group consisting of sulfates, sulfonic acid groups or carboxyl groups.

23. A method as claimed in claim 21, wherein said vascularizing compound consists of acrylic acid, methacrylic acid, crotonic acid, itaconic acid, vinylsulfonic acid or vinylacetic acid.

24. A method as claimed in claim 21, wherein said biocompatible polymer consists of polyacrylates.

25. A method as claimed in claim 21, wherein said vascularizing compound consists of methacrylic acid which is incorporated into the biocompatible polymer at the time of polymerization.

26. A method for increasing blood flow to transplanted cadaverous gum tissue comprising:
   positioning an angiogenic material between the transplanted tissue and a host tissue along a suture line,
   said angiogenic material consisting of a biocompatible polymer and a vascularizing compound consisting of polymerizable compounds capable of forming anions and which promote the growth of blood vessels, which, when implanted in animal tissue, said angiogenic material promotes generation of blood vessels in its immediate vicinity and induces minimal or no fibrous capsule formations.

27. A method as claimed in claim 26 wherein said vascularizing compound consists of a polymerizable compound containing an ionizable group consisting of sulfates, sulfonic acid groups or carboxyl groups.

28. A method as claimed in claim 26, wherein said vascularizing compound consists of acrylic acid, methacrylic acid, crotonic acid, itaconic acid, vinylsulfonic acid or vinylacetic acid.

29. A method as claimed in claim 26, wherein said biocompatible polymer consists of polyacrylates.

30. A method as claimed in claim 26, wherein said vascularizing compound consists of methacrylic acid which is incorporated into the biocompatible polymer at the time of polymerization.

\* \* \* \* \*